(12) United States Patent
Loughrey

(10) Patent No.: US 10,682,280 B2
(45) Date of Patent: Jun. 16, 2020

(54) DERMAL APPLICATOR DEVICE

(71) Applicant: CRYOSKIN CARE Ltd., Peacehaven, East Sussex (GB)

(72) Inventor: Tracey Loughrey, Peacehaven (GB)

( * ) Notice: Subject to any disclaimer, the term of this patent is extended or adjusted under 35 U.S.C. 154(b) by 56 days.

(21) Appl. No.: 15/551,584

(22) PCT Filed: Feb. 22, 2016

(86) PCT No.: PCT/GB2016/050441
§ 371 (c)(1),
(2) Date: Aug. 16, 2017

(87) PCT Pub. No.: WO2016/132158
PCT Pub. Date: Aug. 25, 2016

(65) Prior Publication Data
US 2018/0243160 A1    Aug. 30, 2018

(30) Foreign Application Priority Data

Feb. 20, 2015  (GB) .................................. 1502900.2
Feb. 23, 2015  (GB) .................................. 1502906.9

(51) Int. Cl.
*A61H 15/00*    (2006.01)
*A61H 15/02*    (2006.01)
(Continued)

(52) U.S. Cl.
CPC ......... *A61H 15/0092* (2013.01); *A61H 15/00* (2013.01); *A61H 15/02* (2013.01);
(Continued)

(58) Field of Classification Search
CPC .......... A61H 7/00; A61H 7/002; A61H 7/003; A61H 7/007; A61H 2007/009;
(Continued)

(56) References Cited

U.S. PATENT DOCUMENTS 1,947,042 A     2/1934  Glennan
2006/0100558 A1  5/2006  Smith
(Continued)

FOREIGN PATENT DOCUMENTS

FR       2633513 A1 *  1/1990  ............... A61F 7/10
WO   2015/123207 A1     8/2015

OTHER PUBLICATIONS

Search Report dated Dec. 8, 2016 in PCT/GB2016/050441.
Written Opinion dated Dec. 8, 2016 in PCT/GB2016/050441.

*Primary Examiner* — Colin W Stuart
(74) *Attorney, Agent, or Firm* — Young Law Firm, P.C.

(57) ABSTRACT

A dermal applicator device may include a housing having a retainer configured to hold and engage a spherical surface. A reservoir, containing a liquid, is contained within a shell that is at least partially spherical but at least has curved surfaces supporting rotation. The shell may be engaged within the retainer to permit relative rotation of the shell with respect to the housing. The liquid may be selected to have a freezing point below 0° C. and/or a specific latent heat of fusion higher than water. The shell may further include an outwardly protruding lug extending from its surface, and the housing may be configured to form an orbital chamber between an inner surface thereof and the shell when the shell is retained in the retainer. The protruding lug is constrained within the orbital chamber such that rotation of the shell relative to the housing is restricted.

15 Claims, 3 Drawing Sheets

(51) Int. Cl.
*A61M 35/00* (2006.01)
*A45D 34/04* (2006.01)
*A45D 40/26* (2006.01)

(52) U.S. Cl.
CPC .......... *A61M 35/003* (2013.01); *A45D 34/04* (2013.01); *A45D 34/041* (2013.01); *A45D 40/26* (2013.01); *A45D 40/261* (2013.01); *A61H 2015/0042* (2013.01); *A61H 2015/0064* (2013.01); *A61H 2201/02* (2013.01); *A61H 2201/0214* (2013.01); *A61H 2201/0257* (2013.01); *A61H 2205/022* (2013.01)

(58) Field of Classification Search
CPC .... A61H 15/00; A61H 15/0092; A61H 15/02; A61H 2015/0007; A61H 2015/0028; A61H 2015/0042; A61H 2015/0057; A61H 2015/0064; A61H 2015/0071; A61H 2201/02; A61H 2201/0207; A61H 2201/0214; A61H 2201/0221; A61H 2201/0264; A61H 2201/0257; A61H 2205/022; A61M 35/003; A45D 34/00; A45D 34/04; A45D 34/041; A45D 40/26; A45D 40/261; A45D 40/28; B65D 47/268; B65D 39/06
USPC .......................... 222/167, 237, 548, 556, 452
See application file for complete search history.

(56) References Cited

U.S. PATENT DOCUMENTS

| | | | |
|---|---|---|---|
| 2008/0154161 A1* | 6/2008 | Abbott | A61H 15/0092 601/113 |
| 2008/0154162 A1* | 6/2008 | Thiebaut | A61H 7/003 601/125 |
| 2010/0087763 A1* | 4/2010 | Hane-Karr | A61H 7/007 601/137 |
| 2012/0238926 A1* | 9/2012 | Diezinger | A45D 34/041 601/154 |
| 2014/0228723 A1* | 8/2014 | Cockerill | A61H 15/0092 601/128 |
| 2015/0223970 A1* | 8/2015 | Holland | A61F 7/10 601/19 |

* cited by examiner

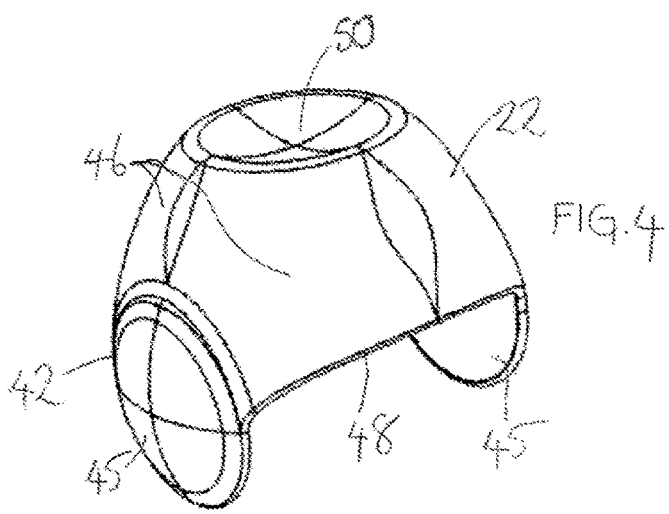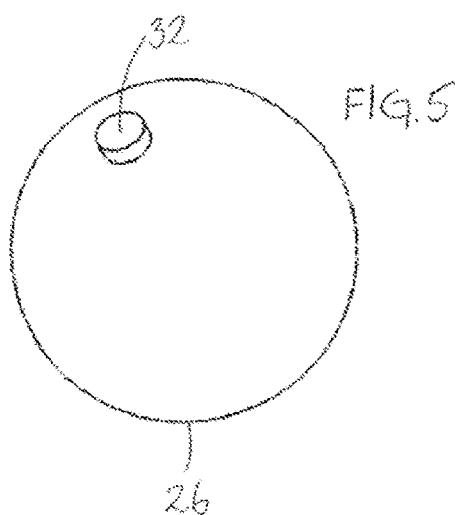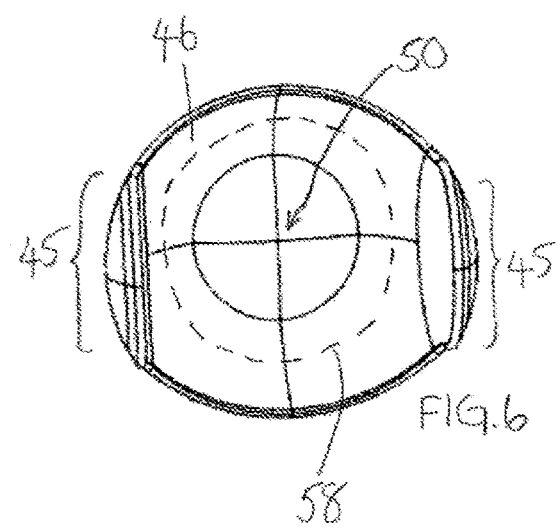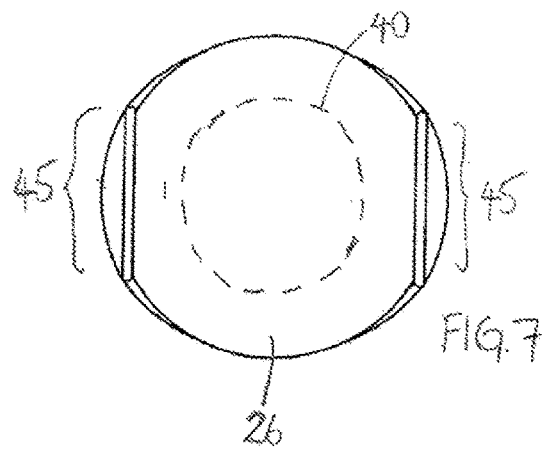

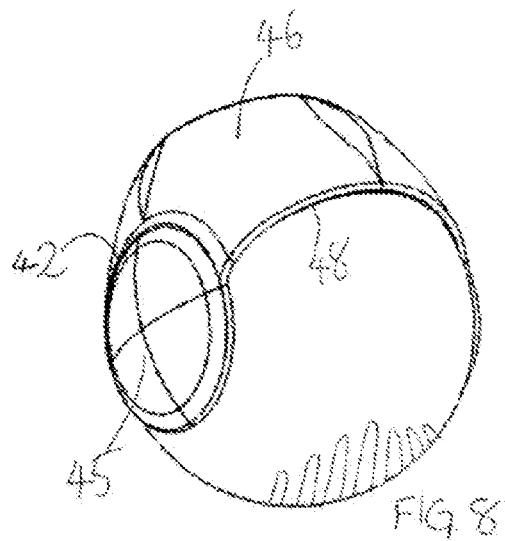
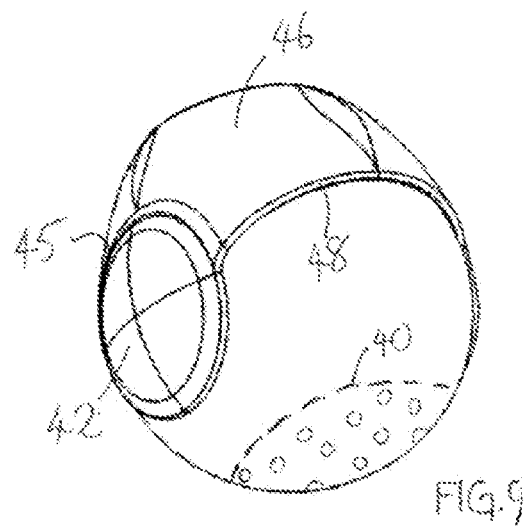
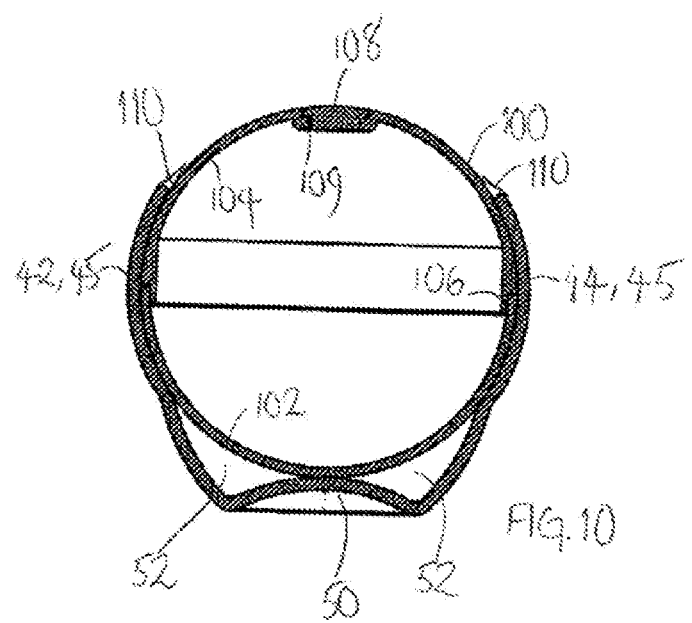

DERMAL APPLICATOR DEVICE

BACKGROUND

This invention relates, in general, to a device for treatment of the skin particularly but not exclusively to facilitate application of dermal compositions, especially skin treatment formulations for medical or cosmetic purposes. This invention finds particular application in dispensers for formulations which are applied facially, although the applicator of the invention may be used on other areas of the human body.

The device may also find application in the preparation and/or treatment of skin to improve vascular microcirculation in the skin tissue and thereby promote absorption of subsequently applied skin treatment formulations.

FR2679131 discloses a cryogenic massager comprising a hollow roller with an insulated handle.

SUMMARY

According to a first aspect of the present invention there is provided a dermal applicator device comprising: a housing having a retainer configured to hold and engage positively a spherical surface; and a reservoir containing a liquid, the reservoir contained within a shell that is at least partially spherical and which shell is configured to be engaged within the retainer to permit relative rotation of the shell with respect to the housing, the liquid having at least one of: i) a freezing point below 0° C. and (ii) a specific latent heat of fusion higher than that of water.

Preferably, the shell further includes an outwardly protruding lug extending from its surface and the housing is configured to form an orbital chamber between an inner surface thereof and the shell when the shell is retained in the retainer, the protruding lug constrained within the orbital chamber such that rotation of the shell relative to the housing is restricted.

The liquid may comprise a salt solution, a gel or a polyol.

In another aspect of the present invention there is provided a kit of parts containing a plurality of interchangeable dermal applicator components, the set comprising: a housing having a retainer configured to hold and engage positively a reservoir having a surface; and a plurality of reservoirs each containing one of a liquid, each reservoir having a shell that is at least partially curved and which shell is configured to be engaged within the retainer to permit relative rotation of the shell with respect to the housing, wherein the liquid within each reservoir has at least one of (i) a freezing point below 0° C. and (ii) a specific latent heat of fusion higher than that of water and wherein cooling properties exhibited by each of the plurality of reservoirs varies from one to another based on at least one of: i) a composition of the liquid; and ii) the construction of the shell.

At least one of the shells of the different reservoirs may further include an outwardly protruding lug extending from its surface and the housing is configured to form an orbital chamber between an inner surface thereof and the shell when the shell is held by the retainer and retained in the housing, the protruding lug constrained within the orbital chamber such that rotation of the shell relative to the housing is restricted.

In a further aspect of the invention there is provided a housing and a dermal contact member rotatably engageable within a socket in the housing; wherein the dermal contact member comprises a shell, a reservoir internal to the shell for retaining liquid and a filler cap for closing the reservoir; the shell having a spherical outer contact surface; the housing comprising a hand grip and a plurality of resilient hub members, the hub members defining a socket within which the contact member may be releasably engaged permitting restricted angular rotational movement of the contact member within the socket; the contact member being releasable from the socket to permit filling or emptying of liquid in the reservoir.

Use of a dermal treatment device in accordance with the present invention confers numerous advantages. A plurality of contact members may be used with a single housing and hand grip, so that a supply of cold contact members may be available for successive replacement and use. The device may be used for a stimulation facial massage. Freezing cold temperatures cause vasoconstriction and vasodilation which encourage vascular micro circulation in the skin tissue. Application of cosmetic or medicinal agents is facilitated. Use of the device promotes relaxation, improved skin firmness and radiance. Tightened pores and significantly firmer tissue may be achieved and fine lines, wrinkles and facial redness may be reduced.

Further applications for the device include pre- and post-treatment of inflammation caused by burns, hair removal and tattooing as well as site preparation or soothing respectively before or after administration of an injection.

The restricted movement of the contact member reduces wastage of skin treatment composition, and surplus composition may be gathered by the presence of convex scraping surfaces that capture excess composition as the direction of rotation is changed. However, in one embodiment, restriction of orbital movement of the shell within the housing reduces the likelihood of (typically) skin-applied, roller-coated surplus composition to be rotated under the housing and thus lost beneath the housing.

In a first method, the contact member is rolled or caused to slide over the skin on a portion of the user's face or other region of the body. Contact with the chilled spherical surface causes vasoconstriction or vasodilation increasing circulation of the dermal tissue. Furthermore, contact with the cold surfaces causes contraction of skin cells creating spaces between the cells to improve absorption of a subsequently applied medicinal or cosmetic composition.

In a second or subsequent method, a medicinal or cosmetic composition is applied to the skin or to the contact surface followed by rolling of the contact member across the skin to cause the composition to be distributed and absorbed across the skin.

In still yet another aspect of the invention there is provided a process of lowering a temperature of a selected local area of skin to increase a rate of absorption of a topically applied composition, the method comprising: selecting at least one reservoir from a kit of reservoirs and chilling said selected at least one reservoir; selecting one chilled reservoir and loading the reservoir into a housing of dermal applicator device as recited in claim 1; and massaging an area of skin with the dermal applicator device to cause rotation of the shell against the skin and relative to the housing, wherein heat is drawn from the skin through the shell to support over time an increase in heat of contents in the reservoir and, should the content in the reservoir initially be a frozen liquid, a phase-state transition of the contents held within the chilled reservoir.

Reservoirs may be chilled to different temperatures so that progressive cooling may be applied to a subject based, for example, on selective changing of the reservoir in use. For this purpose, a kit of reservoirs may contain different liquids with different freezing points or different thermal capacities, and/or the physical properties of the reservoirs may be altered.

The invention is further described by means of example but not in any limitative sense with reference to the accompanying drawings of which:

BRIEF DESCRIPTION OF THE DRAWINGS

FIGS. 4 and 5 show a preferred embodiment of a housing of the dermal treatment device of FIG. 1, the housing disassembled from a spherical reservoir of FIG. 5

FIG. 6 shows a top plan view of the dermal treatment device of FIG. 1, including an indication of an orbital channel shown in dotted outline;

FIG. 7 shows a bottom plan view of the dermal treatment device of FIG. 1, including a region of preferred contact points shown in dotted outline;

FIGS. 8 and 9 show in situ alternative embodiments of the spherical reservoir of FIG. 5; and FIG. 10 shows, in cross-section, an alternative embodiment for construction of a spherical reservoir.

DESCRIPTION

Figure 1:
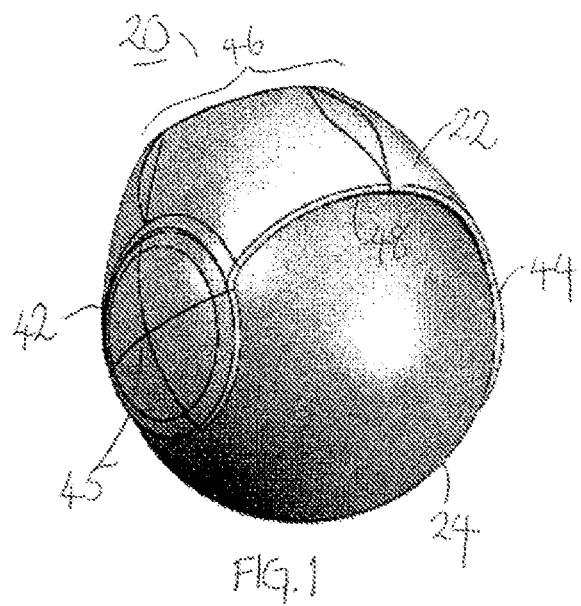
FIG. 1 is an isometric view of preferred embodiment of a dermal treatment device.

With reference to FIGS. 1 to 5, there is shown a preferred embodiment of a dermal treatment device 20. The device 20 includes a housing 22 and a generally spherical reservoir 24 (or, interchangeably, "contact member") comprised from a relatively thin shell 26 of material, such as (not limited to) a polymeric material in the form of a blow-molded polypropylene or other polyolefin, a synthetic resin, a metal or a ceramic. Manufacture of the contact member from metal, ceramic or stone is less preferred, due to a potential risk of causing frost burns or at least an excess of chilling that is either undesirable or uncomfortable.

The reservoir is filled with a liquid, such as a salt solution, or otherwise a gel or a polyol 28. The liquid or gel 28 in the reservoir is preferably a liquid with a low freezing point, for example saline, magnesium sulphate solution or calcium chloride solution or an alkylene glycol or polyol, such as glycerol. The liquid or gel 28 may be selected to have a high specific latent heat of fusion. The liquid of gel 28 serves as a heat sink. Therefore, by placing the relatively cold, thermally-conductive surface of the shell in contact with the dermis, heat is transferred away from the dermis and sunk into the liquid or gel within the reservoir. The liquid or gel in the reservoir is selected such that any phase transition (should the liquid or gel be initially frozen) is relatively slow, with this preferable physical property resuting in maintainence of a relatively cold contact surface temperature at the shell for an extended working period. Maintaining a temperature differential and, in fact, maintaining a relatively low temperature on the shell has been found to beneficially promote dermal penetration and/or absorption during massage or other contact by the shell on the skin during an application cycle. Maintenance of a stable and relatively low temperature is important, so selected liquids or gels, although typically aqueous based, will have superior thermal characteristics to water or homogesous solid blocks of material.

The contact member 24 is preferably partially or wholly spherical, or at least hemispherical. Once filled, the preferably ball-like contact member 24 may be permanently sealed with a plug 30, which in a preferred embodiment extends outwardly to realize an outwardly extending lug 32. The plug 30 and indeed the lug 32 may be formed at and on the injection point, i.e. the gate region produced by the mold during formation of the plastic part. The plug and/or lug may be achieved with a simply thermal crimping procedure. Alternatively, the plug 30 may realize a separate and discretely manufacturable filler cap—which can be considered to be the combination of plug 30 and lug 32—that permits the liquid or gel 28 that is stored in the reservoir to be changed, as desired.

Shell material and thickness are preferably optimized for heat transfer, although shape integrity is important to maintain when the shell is under pressure arising from the application of force applied through the housing during rolling of the device on the skin.

However, it is preferred that the contact member 24 is entirely sealed and the contact member 24 treated as a replaceable component within a set. The dermal treatment device may therefore be provided as a kit of parts, which set includes a plurality of interchangeable contact members 24 having slightly different heat capacity profiles for the liquids or gels. Differing freezing points and/or different thermal transmission properties may be used to regulate or control the cooling effect for the device over a predetermined operative period of time for a particular selected contact member within the set, with different contact members selectable for use with different parts of the skin. For example, use of the dermal device on the face may make use of a different spherical contract member relative to treatment of, say, the buttocks or indeed the feet.

The kit may comprise shells with different diameters together with appropriate housings. The shell may be non-spherical, such as being egg-shaped. The shells may have a contact area that has a different radius relative to other parts of body of the reservoir. The shells, however, will all contain some form of curved surface to allow for rotation. Unless the context requires a different and more limited interpretation, the term spherical should therefore be understood as a functional term to mean a shape having one or more curved surface that are designed to support relative rotation within the housing and/or against the skin and not merely a shape that has a substantially circular cross-section. Clearly, a substantially spherical reservoir provides many degrees of movement and, in general, is considered superior because, for example, it is relatively easy to mold.

Figure 2:
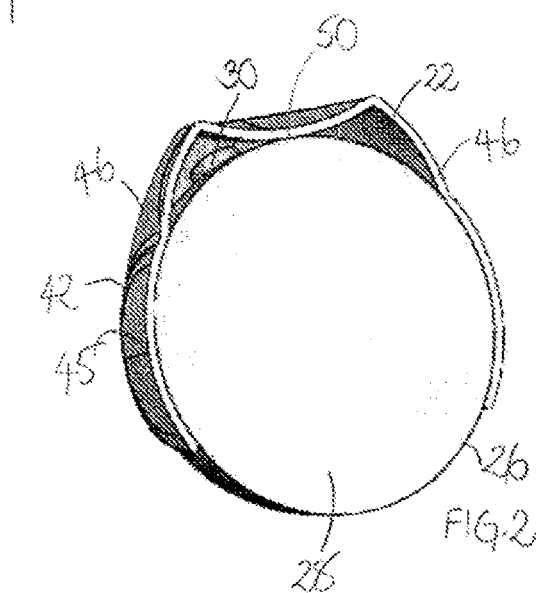
FIGS. 2, 3a and 3b cross sections through the dermal treatment device of FIG. 1 and taken from the perspectives of an isometric view and a front view.
Figure 3A:
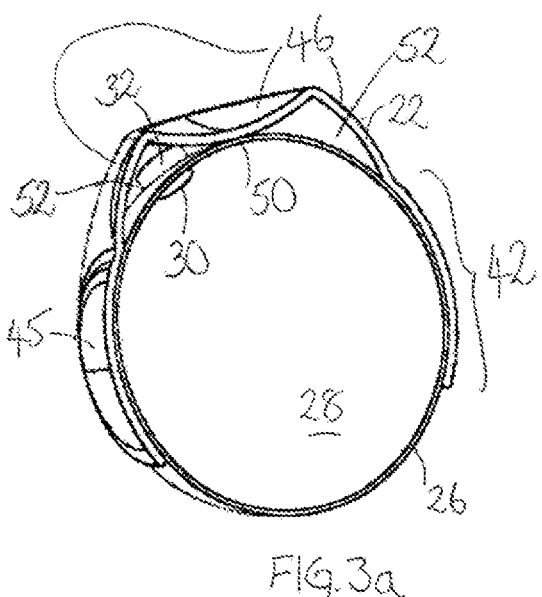
Figure 3B:
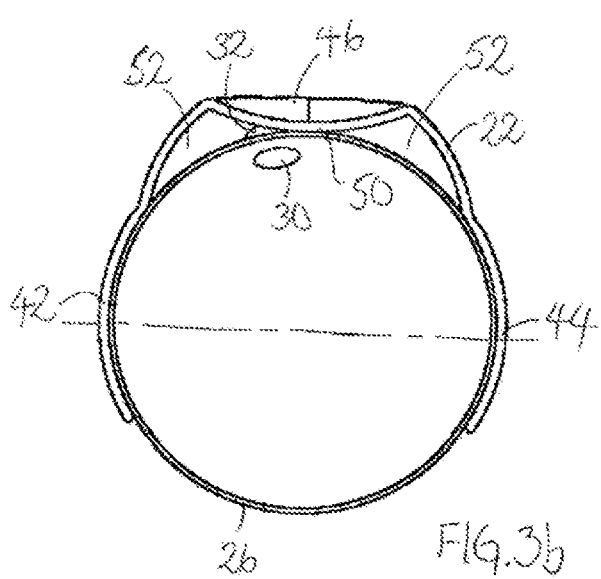

In a preferred embodiment the shell 26 of the contact member is 24 is substantially spherical, having a spherical contact surface. As shown in FIGS. 2, 3 and 5, the lug 32 extends from the surface of the contact member in a direction diametrically generally opposed to a working contact surface (that comes into contact with the skin of the user). The working contact surface may typically comprise a limited portion of the surface of the shell 26 which contacts a subject's skin when the contact member is pressed against a user's skin during use. The working contact area is shown by a dotted line border in FIGS. 7 and 9 and indicated by reference number 40.

Returning to FIG. 1 and FIG. 4 (especially), the housing 22 is preferably comprised of a plastic cap that clasps the contact member 24 lightly on, near or around the circumference of the contact member 24. The contact allows for relatively free rotation—there may preferably be some degree of resistance to movement, rather than an entirely free-spinning arrangement—of the contact member 24 relative to the housing 22.

Preferably two hub members 42, 44 are separated from each other through a connecting bridge member 46. The two hubs—similar to forks on a bike frame or, indeed, fingers of a hand—are typically located on diametrically opposite sides of the contact member 24 (or may be equidistantly-spaced around the circumference) and produce a socket. Typically, to realize the socket, each hub member 42, 44 includes, at its end, a retainer cup 45 (or retaining spring clip, resilient member or the like) that is arranged to receive and engage a part of the spherical contact surface of the contact member 24, thereby retaining the spherical contact member between the hubs but allowing for its rotational movement within the sockets. The retainer cap is therefore integral to each hub, although it is described separately for reasons of explaining the function that the parts respectively perform. The bridge member, linking the hubs 42, 44 together, preferably provides resilience to allow the dermal contact member, e.g. the shell 26 containing the reservoir, to be snapped into and out of the retainer cups.

In preferred embodiments, the housing comprises an axially extending body with two hubs forming lobes on either side of the socket.

The bridge member 46 covers an upper portion of the contact member 24 and thereby provides structure which serves as a hand grip. The bridge member may include scalloped edges that reduce its overall coverage and expose the shell 26 of the contact member 24. The bridge member 46—as well as the hum hub members—is preferably an insulated plastic material that is cap-shaped and of a generally hemispherical geometry, and is shape-configured such that the cap can fit within a hand of the person using the device. The cap therefore insulates the reservoir from heat from the hand. In some respects, the overall shape of the hand grip resembles, in appearance, a leather aviation helmet or cap with ear-flaps.

Alternatively, the contact member may be engaged between three or four hub members, typically arranged symmetrically around the circumference of the at least partially spherical contact surface. These hubs may form a close fit to grip lightly the contact member 24 in the same way as a fingers of a hand might pick up an apple. Of course, the points of contact are described as being located about the circumference, although the number, location and size of the retainer caps that engage the shell 26 are deterministic and can be changed, as will be understood, based on design considerations known to the skilled addressee.

In either case, the freedom of the ball, i.e. the contact member 24, to rotate within the housing is controlled by the clearances within the complete housing/ball assembly and particularly the degree of grip exerted by the retainer cups 45 at or near the circumference. Typically, the housing is therefore also a hollow shell with an internal abutment surface arranged to engage the upstanding lug 32 thus preventing further rotation of the contact member 24. Abutment of the lug 32 against the interior surfaces of the housing—especially the channel 52 formed between the housing and the contact member by virtual of the housing's geometry—allows limited rotational movement of the contact member within the housing as the device passes across a subject's skin.

In a preferred embodiment, an upper part of the bridge is formed to include a central dip 50 that is closely displaced to (or in abutment with) the contact member 24 near its summit. Surrounding the dip, a discrete circumferential channel 52 is formed, which channel 52 extends a portion of the way down each hub 42, 44 before coming into close proximity (if not limited abutment) to the contact member 24 at or in the vicinity of each retainer cap. Typically, the channel 52 is limited to an upper hemisphere of the housing 22 and is dimensioned to allow the lug 32 to move within the channel 52. The channel 52 therefore defines an orbit—reference numeral 58 of FIG. 6—of restricted rotation of the contact member 24 within the housing 22. The geometry of the channel may not define a full orbit, but sensibly the channel forms an annulus around a pole/major axis through the device from top to bottom. Consequently, the restricted movement of the lug 32 therefore also produces a corresponding restriction in the amount of contact achievable by a generally perpendicular orientation of the device 20 relative to the skin being rolled or massaged. This limited contact achieved at the bottom of the spherical contact member 24 is illustrated by the dotted border 40 shown in FIGS. 7 and 9.

In particularly advantaegous embodiments, the area and dimensions of the contact surface may be controlled by abutment of the filler cap against an interior surface of the housing. With the housing having a hollow interior, a peripheral abutment surface is configured to control, in use, the extent and direction of rotation of the spherical surface in. A larger diameter lug 32 will reduce the available freedom to move in comparison to a contact member 24 exhibiting a smaller diameter lug.

Use of a reduced and restricted contact area 40 (on the contact member 24) is advantageous when a high value cosmetic composition is employed, or if a potent medicinal composition for which the dosage must be regulated is administered.

Functionally, the housing therefore provides a handgrip that facilitates application of pressure by the contact surface against a user's skin during use. The handgrip is preferably axially symmetrical with respect to an axis extending through the point of contact of the spherical contact surface with a user's skin. Use of the handle prevents a user's fingers from becoming cold during use or otherwise be exposed to chemical ingredients of, or active reagent in, the composition being applied.

A preferred axially symmetric construction of the housing (as a handle) allows a user to roll the device in any direction using either hand. This facilitates application to both sides of a user's face without need to manipulate the operators grip on the housing. Preferably the device is moved across a subject's skin in small circular rotations. Of course, the housing 22 could be ergonomically-shaped to a particular hand.

A kit in accordance with this invention may include two or more differently dimensioned housings to allow for comfortable and accurate use by different users.

The shell's surface on the contact member may be smooth or may be provided with one or more indentations, projections or channels configured to control application of a treatment composition to a subject's skin. Projections are not preferred since these require increased clearance requirements in the event that the contact member is freely revolving and unrestricted; this embodiment will be described later with reference to FIG. 10. Alternatively, or in addition, the surface may be porous, for example having a porous or sponge-like outer surface with an underlying rigid structure.

Referring briefly to FIGS. 8 and 9, these figures show embodiments of the device 20 that include a textured outer surface, with the texture realized by lateral channels or circular crevices formed at least in a base region of the contact member 24. The concentration of these channels and/or the size and or the shape of these channels and crevices (or protrusions) may vary across the surface region or may have a uniform distribution. For example, channels or features in the surface of the contact member may vary in depth, width, spatial arrangement or density. The benefit of the use of texture (e.g. channels, grooves, recesses, protrusions or the like) is that they can act to retain some of the composition in the immediate vicinity of the contact point and, indeed, the tip of the contact member 24, thereby allowing this to be worked into the skin without having to overdose the area.

Furthermore, the restricted movement of the spherical contract member means that a cream or gel composition—topically applied to the treatment area—will generally be worked into the skin under treatment alone, and will not be rolled under the housing by virtue of full unrestricted rotation of the contact member 24. Of course, with accurate dimensioning and selectively applied limiting clearance, edges of the housing (such as along the scallop portion 48) can act as cleaning scrapers that collect the cream or gel for re-use and prevent the cream or gel being lost and wasted underneath the housing. The housing may therefore comprise an outer skin with edges which form a scraping contact with the surface of the spherical contact member 24. The scraping contact, which may be a flexible blade, allows removal of excess composition from the surface of the contact member and prevents the composition from being spread over the entire surface of the contact member during use. In a preferred embodiment the housing comprises a pair of opposed hub members with a concave surface extending on either side between the hub members. The concave surface serves to gather surplus treatment composition allowing redistribution by rotation of the contact member when the direction of movement of the contact member is reversed or changed.

Referring to an alternative construction of the contact member (shown in FIG. 10), this contact member may again held with the housing previously described. However, as can be seen for the cross-section, the contact member 100 is assembled by the sealing together of two hemispherical domes 102, 104. This sealing may be achieved with heat or a bonding agent, with alignment assisted by an operative pair of a complementary lip and step 106 formed in edges of the two hemispherical domes 102, 104. To allow full three hundred and sixty degree rotation of the contact member 100, there is no lug 32 (as shown previously in FIG. 5), but rather a plug 108 having, typically, a circular arrangement. The plug 108 fits flush into the surface of one of the two hemispherical domes, thereby allowing a fill port 109 to be stoppered. The plug 108 may be permanently secured in place, or may release with the use of a tool. With this arrangement, the use of flexible plastic scrapers 110 is considered more important, since these thin and flexible blades are designed to abut against and lightly engage the surface of the contact member so as to accumulate composition that might otherwise work its way beneath the cap and be lost from use (or inhibit rotation of the contact member within the housing). The scrapers 110, as shown, may be of a plastic material (or the like) and are located along the edges of the housing and fixed in place by means of an adhesive, by a deformable features and mechanically, such as through use of some form of pinning or tongue and groove arrangement.

In specific instances where the contact member 24 includes a porous shell, the fill port provides a mechanism for replenishing lost reservoir liquid or gel. The reservoir liquid or gel 28 may, in very specific circumstances, itself form part of the dermis stimulation or skin treatment and, consequently, may be formulated accordingly.

In terms of set-up and use, the contact members will typically be placed in a refrigerator or preferably a freezer to allow the liquid or gel 28 to be reduced in temperature, if not frozen. The contact member 24 is typically cooled to a convenient operating temperature, typically 0° C. to −15° C. The contact member can then be snapped into the housing 22. As indicated above, the cream or treatment composition is typically then applied topically to the skin area, although it could be applied directly to the contact area 40—which might be marked with a line or physical boundary—and the device worked/massaged over the skin area. Small rotational movements may be preferred.

Through a thermal conduction process via the shell 26, the liquid or gel 28 in the reservoir serves as a heat sink to facilitate heat transfer away from the contact surface and, indeed, in area of the body in which the rotatable shell is in contact. The skin may be prepared, first, with a cold treatment with the device and then a cosmetic or medicinal composition can be applied with the same device (or otherwise with new contact member taken straight from cold storage). It is envisioned that the application process can take several steps of different creams or compositions.

Use of the dermal applicator device may therefore also be viewed from the perspective of a process for lowering a temperature of a selected local area of skin to increase a rate of absorption of a topically applied composition.

Besides cosmetic treatments with gels and creams, the dermal applicator device of the present invention may be used in a number of other applications, including (but not limited to) the treatment of burns, hair removal, the preparation of sites for tattooing, the de-sensitising of skin before injections and/or the pre- or post-treatment of inflammation, generally.

It will be further understood that unless features in the particular preferred embodiments are expressly identified as incompatible with one another or the surrounding context implies that they are mutually exclusive and not readily combinable in a complementary and/or supportive sense, the totality of this disclosure contemplates and envisions that specific features of those complementary embodiments can be selectively combined to provide one or more comprehensive, but slightly different, technical solutions. To illustrate interchangeability between hardware arrangements and design options for specific structural shapes, components have been described generally in terms of their functionality and intended usage.

It will, of course, be appreciated that the above description has been given by way of example only and that modifications in details may be made within the scope of the present invention. For example, whilst a preferred embodiment has been described in the context of the single hand-held device, other scaled sizes are possible. For example, the housing may be configured in the form of a pen in which the tip is enlarged to accommodate a scaled reservoir. Dimensional sizing may therefore be considered to be determined by application, with smaller spherical reservoirs providing more localized control and targeted use. Of course, with decreasing spherical radii, heating of the reservoir liquid (or gel) is potentially more rapid, so sizing is generally selected to provide general precision and a use time sufficient to allow for the topical composition to be worked effectively into the dermis, and more typically the papillary region and the reticular dermis. Additionally, although the contact member is preferably realized by a hollow sphere having a reservoir filled with a particular liquid, the ball could be constructed in the form of a solid having selected thermal characteristics. Of course, using a liquid or gel arrangement is preferred, since maintenance of a uniform temperature and longevity of relative coldness are better regulated through the shell.

By way of further implementation, a single retainer clasp shaped to the diameter of contact member and assembling a portion of a curved annulus could be used, rather than the pair of diametrically opposing retained disclosed above and shown in FIG. 1 (for example). In this instance, the rotating ball would be retained in place and engaged by the single retainer clasp. Disassembly of the contact member, i.e. the chilled spherical reservoir hollow ball, from the housing could be achieved either by two processes. First, assuming that the single retainer clasp extends more than one hundred and eight degree around the circumference and, preferably, at least about two hundred and twenty degrees, then release and replacement of the contact member may again be based on a snap lock arrangement and the overcoming of a resistive force within the single retainer clasp (that is suitably integrated into a housing). An alternative arrangement could see the housing assembled from a pair of parts that are held together along an interface by a locking clasp. In the latter respect, release of the locking clasp (or its functional equivalent, e.g. one or more screws into one or corresponding threads) would allow for the separation of the two halves of the housing and therefore access to the contact member (for cleaning or replacement). The housing could still include the channel 52 for restricting orbital movement of any lug extending from the contact member, as described. In having an arrangement in which the housing is effectively hinged, the fingers of the housing no longer need to be spring-like in their retaining action, although movement of the chilled reservoir ball is preferably not entirely freewheeling but rather requires some limited work to be done to overcome any contact or spring force at a retainer that holds the reservoir ball generally in place within the housing.

The invention claimed is:

1. A dermal applicator device comprising:
   a housing having a retainer configured to hold and engage a spherical surface; and
   a reservoir containing a liquid, the reservoir contained within a shell that is at least partially spherical and which shell is configured to be engaged within the retainer to enable relative rotation of the shell with respect to the housing, the liquid having at least one of:
   i) a freezing point below 0° C. and (ii) a specific latent heat of fusion higher than that of water,
   wherein the shell further includes an outwardly protruding lug extending from its surface and wherein the housing is configured to form an orbital chamber between an inner surface thereof and the shell when the shell is held by the retainer and retained in the housing, the protruding lug being constrained within the orbital chamber such that rotation of the shell relative to the housing is restricted.

2. The dermal applicator device according to claim 1, wherein the shell comprises an outer covering that is smooth.

3. The dermal applicator device according to claim 1, wherein the shell comprises an outer covering that, at least over part of its surface, includes a texture effect.

4. The dermal applicator device according to claim 1, wherein the housing is a thermal insulator and wherein at least part of an outer edge of the housing adjacent the shell forms or contains a scraper element.

5. The dermal applicator device according to claim 1, wherein the lug forms part of a releasable plug that stoppers a fill port to the reservoir.

6. The dermal applicator device according to claim 1, wherein the retainer includes at least two displaced retainer cups that engage against an outer surface of the shell and between which is rotatably clamped the shell, the at least two retainer cups being connected together through a bridge that that forms part of the housing and that defines an upper part of the dermal applicator device.

7. The dermal applicator device according to claim 6, wherein the bridge is configured as a spring to resist spacing apart of the at least two displaced retainer cups.

8. The dermal applicator device according to claim 1, wherein the liquid is selected from the group consisting of:
   a salt solution;
   a gel; and
   a polyol.

9. A kit of parts containing a plurality of interchangeable dermal applicator components, the kit of parts comprising:
   a housing having a retainer configured to hold and engage a reservoir having a surface; and
   a plurality of reservoirs each containing a liquid, each reservoir comprising a shell that is at least partially curved and that is configured to be engaged within the retainer to enable relative rotation of the shell with respect to the housing, wherein the liquid within each reservoir has at least one of: (i) a freezing point below 0° C. and (ii) a specific latent heat of fusion higher than that of water and wherein cooling properties exhibited by each of the plurality of reservoirs varies from one to another based on at least one of:
   i) a composition of the liquid; and
   ii) the construction of the shell,
   wherein at least one of the shells of the plurality of reservoirs further includes an outwardly protruding lug extending from its surface and the housing is configured to form an orbital chamber between an inner surface thereof and the shell when the shell is held by the retainer and retained in the housing, the protruding lug being constrained within the orbital chamber such that rotation of the shell relative to the housing is restricted.

10. The kit according to claim 9, wherein the liquid in each of the plurality of reservoirs comprises one of a salt solution, a gel and a polyol.

11. A dermal treatment device, comprising:
   a housing having a retainer configured to hold and engage a spherical surface;
   a dermal contact member rotatably engageable within a socket in the housing, the dermal contact member comprising a shell, a reservoir internal to the shell and configured to retain liquid and a filler cap configured to close the reservoir, wherein:
   the shell comprises a spherical outer contact surface;
   the housing comprises a hand grip and a plurality of resilient hub members, the plurality of resilient hub members together defining a socket within which the contact member is releasably engaged to enable restricted angular rotational movement of the contact member within the socket; and
   the contact member is releasable from the socket to enable the reservoir to be filled or emptied of liquid,
   wherein the shell further includes an outwardly protruding lug extending from its surface and wherein the housing is configured to form an orbital chamber between an inner surface thereof and the shell when the shell is held by the retainer and retained in the housing, the protruding lug being constrained within the orbital chamber such that rotation of the shell relative to the housing is restricted.

12. The dermal treatment device according to claim 11, wherein the outer contact surface is smooth.

13. The dermal treatment device according to claim 11, wherein the outer contact surface is, at least over part of its surface, textured.

14. The dermal treatment device according to claim 11, wherein the housing comprises a thermal insulator material and wherein at least part of an outer edge of the housing adjacent the shell forms or contains a scraper element.

15. A process of lowering a temperature of a selected local area of skin to increase a rate of absorption of a topically applied composition, the method comprising:

selecting at least one reservoir from a plurality of reservoirs, each containing a liquid and each having a shell that is at least partially curved, wherein the liquid within each reservoir has at least one of: (i) a freezing point below 0° C. and (ii) a specific latent heat of fusion higher than that of water and wherein cooling properties exhibited by each of the plurality of reservoirs varies from one to another based on at least one of a composition of the liquid and the construction of the shell;

chilling said selected at least one reservoir;

selecting one chilled reservoir and loading the chilled reservoir into a housing of a dermal applicator device, the housing having a retainer that is configured to hold and engage the at least partially curved shell of the loaded chilled reservoir to enable relative rotation of the shell with respect to the housing, the shell further includes an outwardly protruding lug extending from its surface and the housing being configured to form an orbital chamber between an inner surface thereof and the shell when the shell is held by the retainer and retained in the housing, the protruding lug being constrained within the orbital chamber such that rotation of the shell relative to the housing is restricted, and massaging or contacting an area of skin with the dermal applicator device to cause rotation of the shell against the skin and relative to the housing, wherein heat is drawn from the skin through the shell to support, over time, a phase-state transition within the chilled reservoir.

* * * * *